United States Patent [19]

Nakamura et al.

[11] Patent Number: 5,676,957
[45] Date of Patent: Oct. 14, 1997

[54] SKIN EXTERNAL AGENT

[75] Inventors: Norihira Nakamura; Junichi Akiyama, both of Kobe, Japan

[73] Assignees: Nippon Socea Kabushiki Kaisha, Osaka; Kabushiki Kaisha Vimake, Kobe, both of Japan

[21] Appl. No.: 683,697

[22] Filed: Jul. 18, 1996

Related U.S. Application Data

[63] Continuation of Ser. No. 367,011, Dec. 30, 1994, abandoned.

[51] Int. Cl.$^6$ ............................... A61K 9/06; A61K 7/00
[52] U.S. Cl. ........................ 424/401; 424/195.1
[58] Field of Search .......................... 424/195.1, 401

[56] References Cited

U.S. PATENT DOCUMENTS

| | | | |
|---|---|---|---|
| 4,742,046 | 5/1988 | Bliah | 514/8 |
| 5,096,697 | 3/1992 | Adachi et al. | 424/47 |

FOREIGN PATENT DOCUMENTS

| | | |
|---|---|---|
| 3-190809 | 8/1991 | Japan. |
| 5-92990 | 4/1993 | Japan. |

OTHER PUBLICATIONS

Derwent Abstracts 91–286062, "External Skin Agent" (1991).

*Primary Examiner*—Frederick Krass
*Attorney, Agent, or Firm*—Faegre & Benson

[57] ABSTRACT

A skin external agent characterized in that an extract of a plant of genus Euonymus such as *Euonymus alata* Sieb., *Euonymus japonica* Thunb. or *Euonymus radicons* Sieb. is contained as an essential ingredient in a base in combination with other ingredients to be added to this kind of the skin external agent as required. The skin external agent of this invention is free from any strong side effects on the human body, has excellent activity to improve the performance of a skin through the activation of the skin and hair-root cells, an effect to grow hair, and excellent moisture retention and an excellent effect to beautify the skin.

21 Claims, No Drawings

SKIN EXTERNAL AGENT

This is a continuation of U.S. patent application Ser. No. 08/367,011 filed 30 Dec. 1994.

BACKGROUND OF THE INVENTION

1. Field of the Invention

This invention relates to a composition of an agent for external use in skin (hereinafter referred to as "skin external agent") which contains, as an essential ingredient, an extract of a plant of genus Euonymus such as *Euonymus alata* Sieb., *Euonymus japonica* Thunb. or *Euonymous radicons* Sieb., which is free from any strong side effects on the human body caused by, for example, a hormone drug, and which is excellent in improving the performance of the skin through the activation of the skin and hair root cells, for growing hair, in retaining moisture and for beautifying the skin.

2. Description of Prior Art

With regard to skin beautification to prevent the skin from aging and the prevention or treatment of spots and freckles as well as the activity to grow hair by the continuous activation of the scalp and the hair roots, many studies on hormone drubs, bloodstream accelerators, various cell-activating ingredients and the like have been so far conducted, and a variety of pharmaceutical ingredients have been produced. However, those having excellent effects and a high level of safety are still few. If the effectiveness of the ingredients which are said to have pharmaceutical effects is objectively evaluated, most of them exhibit only preventive effects, e.g., skin-aging preventive effect.

SUMMARY OF THE INVENTION

This invention has been completed to develop a skin external agent having an excellent level of safety and stability, which beautifies the skin by activating the skin, treats alopecia through a hair growing effect, prevents a person from developing alopecia, and accelerates the performance of the skin and activity to prevent the aging of the skin.

The first object of the present invention is a skin external agent characterized in that an extract of a plant of genus Euonymus such as *Euonymus alata* Sieb., *Euonymus japonica* Thunb. or *Euonymus radicons* Sieb. is contained as an essential ingredient in a base.

The second object of the present invention is a skin external agent characterized in that it comprises a combination of an extract of a plant of genus Euonymus and other ingredients which are known to be contained in an external agent.

Plants of genus Euonymus belong to families Sapindales and Euonymus, and are common in Japan and China. Some of them are planted as garden trees or hedges. These are woody plants that grow in relatively subtropical zones.

Typical examples of the plant of genus Euonymus which is used in this invention are *Euonymus alata* Sieb., *Euonymus japonica* Thunb., *Euonymus radicons* Sieb., and their various species such as *Euonymus japonicus* Thunb. var. aureovariegatus Lowe, *Euonymus japonicus* Thunb. var. longifolius Nakai, *Euonymus japonicus* f. macrophyllus Beiss., *Euonymus boninensis* Koidz., *Euonymus kawachinunus* Nakai, *Euonymus japonicus* f. microphyllus Rehd., and *Euonymus japonicus* Thunb. var. radicifer Nakai.

The extracts of plants of genus Euonymus in this invention can be obtained from the leaves, stems and roots of said plants. The leaves, the stems and the roots may be used either singly or in combination as raw materials for the extract; or ingredients which are extracted separately from the leaves, the stems and the roots may be used in combination as required. The plants as the raw materials for the extract need not necessarily be the plants of one kind, and thus the plants of two or more kinds may be used in combination, such as *Euonymus alata* Sieb. and *Euonymus japonica* Thunb. together.

Regarding the extraction method, for example, a whole portion composed mainly of the stem of *Euonymus alata* Sieb. is chopped, and formed into a semi-fluid liquid with a homogenizer. The squeezed juice can be used either as such or after being concentrated. Preferably, the chopped material of the plant or the semi-fluid liquid of the plant obtained with the homogenizer is extracted with a suitable solvent, and the supernatant solution is evaporated with a freeze drier, after which the extract is incorporated into a base of a skin external agent to prepare a skin cosmetic product or the like.

The extraction solvent includes hydrophilic solvents such as water, ethanol, n-propanol, tert-butanol, propylene glycol and 1,3-butylene glycol, and hydrophobic solvents such as chloroform and diethyl ether. They may be used either singly or in combination. The extraction may be conducted at room temperature or while warming or heating. In the solvent extraction, the plant may be either in its raw form, or in dry or semi-dry form.

The extract obtained via solvent extraction is used by concentration or concentration to dryness as required to facilitate the subsequent processing. At that time, those ingredients contained in the extract which are deemed not to affect activity, such as starch, may be removed via precipitation in a usual manner.

The extract of the plant of genus Enonymus can be contained in a hair-growth skin cosmetic product of this invention in amount of from 0.001 to 10% (W/W), preferably from 0.01 to 5% (W/W) in terms of dry weight (W).

The detailed characteristics of the active ingredient contained in the extract of genus Euonymus, which ingredient is an essential ingredient in the hair-growth cosmetic product of this invention are currently unknown. It is presumed that some of the organic compounds contained in the plant extract, such as sterols, flavonoids, alkaloids, saponins, organic acids and coumarin-type compounds exhibit excellent activity to accelerate the performance of cells as well as excellent moisture retention. It is expected that the extract obtained by using an organic solvent would be substantially lectin free.

The present inventors have extensively studied and developed the activity of extracts of plants of genus Euonymus on hair root cells and skin cells, and have consequently completed this invention.

Activities and effects of the skin external agent in this invention towards skin cells and hair matrix cells were examined using cultured cells and test animals. One of the test examples is described below.

Test Example

The hair on a section of skin from the backs of C3H male mice (6 weeks old) which are ordinarily used as test animals to evaluate the effectiveness of hair-growth activity was completely removed by manual plucking (area approximately 4 cm$^8$). Onto a total of 10 mice in 2 groups (1 group consisted of 5 mice), a 1% *Euonymus japonics* Thunb. extract obtained by dissolving 1% of the extract from leaves and stems of *Euonymus japonicus* Thunb. in a 60% alcohol aqueous solution and a 60% alcohol aqueous solution as a control was applied as test solutions on the hair-removed portion at a dose of 200 microliters once a day until the hair restoration was completed. This applying process was repeated for 25 days.

Twenty hairs were collected from each of the mice on the 13th day, 15th day and 19th day from the day on which the applying with the test solution was started. The lengths of the collected hairs were measured by enlarged measurement, and the effectiveness of the test solutions was examined through total calculations and statistical analysis using a computer.

The results are given in Table 1.

| Group No. (number of mice) | 1 (5) | 2 (5) |
|---|---|---|
| Test solution | 1% *Euonymus japonicus* Thumb. extract | 60% Alcohol aqueous solution as control |
| Average hair length (mm) ± S.D. value | | |
| 13th Day | *2.61 ± 0.13 | *2.36 ± 1.12 |
| 15th day | *4.83 ± 0.23 | *4.24 ± 0.17 |
| 19th day | *6.08 ± 0.15 | *5.44 ± 0.14 |
| Hair thickness (micrometers) | | |
| 13th day | *67.7 ± 0.01 | *56.7 ± 0.0138 |
| 15th day | *68.2 ± 0.0093 | *62.0 ± 0.0064 |
| 19th day | *81.5 ± 0.0106 | *62.0 ± 0.0107 | indicates a significant difference of 1% at a risk ratio given by comparison between both groups according to statistical analysis (t-test).

The results of this test example show that the ingredient of the present invention has an excellent effect of promoting the growth of hair and skin through the increase of the skin performance in the human body.

Details of the mechanisms of action of the ingredient are not known. It is, however, presumed that a certain effectiveness component of the plant extract in the present invention permeates into the skin and causes the activation of the cells of the skin and the hair roots, to accelerate the growth of the capillary vessels that greatly precipitate the growth of hair, to directly increase the performance of the skin cells and to maintain the scalp and hair in good condition. In order to further improve hair-growth accelerating effects by using plants of genus Euonymus in the present invention, the present inventors have studied complex activities provided by a combination of an extract of a plant of genus Euonymus and a substance which has already been known to exhibit a hair-growth effect, such as methyl ester of (3-carboxypropyl)trimethylammonium chloride, 6-amino-1,2-dihydrohydroxyimino-4-piperidinopyrimidine, 7-chloro-3-methyl-2H-benzo-1,2,4-thiadiazine-1,1-dioxide, polyoxyethylene sorbitan monostearate (20 E.O.), an extract solution of *Swertia japonica* Makino, ethinyl estradiol, an extract solution of *Isodon japonica* Hara or an extract solution of a sophora root.

As a result, the present inventors have discovered that the complex of the extract of the plant of genus Euonymus and the known substance which has the hair-growth effect exhibits a synergistic effect of promoting hair-growth by accelerating the skin's performance. This discovery has led to the completion of the second object of the present invention. "20 E.O." means twenty of ethyleneoxide.

Besides the activity given by the complex of the extract of the plant of genus Euonymus and the known hair-growth substance, the present inventors have also studied the activity of the external agent such as in terms of hair-growth acceleration provided by a combination of the extract of the plant of genus Euonymus and a know ingredient such as an ingredient having skin-stimulation activity, an ingredient having cholinergic activity, an ingredient having adrenalin controlling activity or an ingredient having activity to relax the smooth muscle of blood vessels. Consequently, they have found high effectiveness of these ingredients as well.

They have further found an increase in the effect which is considered to be ascribable to an increase in the absorption into the skin that is caused by incorporating into the external agent of this invention a wetting agent, a keratin softening agent and a surfactant which are ordinarily used in cosmetics.

The concentration of the extract of the plant of genus Euonymus used in the skin external agent of this invention is preferably from approximately 0.01 to 5.0%. The concentration of methyl ester of (3-carboxypropyl) trimethylammonium) chloride which is incorporated in a hair-growth accelerator containing from 0.01 to 5.0% of the extract of the plant of genus Euonymus is preferably from approximately 0.01 to 5.0%. Likewise, the concentration of a 6-imino-1,2-dihydrohydroxy-imino-4-piperidinopyrimidine is preferably from 0.01 to 5.0%. The concentration of 7-chloro-3-methyl-2H-benzo-1,2,4-thiadiazine-1,1-dioxide is preferably from approximately 0.01 to 5.0%. The concentration of polyoxyethylene sorbitan monostearate (20 E.O.) is preferably from approximately 1.0 to 60.0%. The concentration of the extract solution of *Swertia japonica* Makino (1 g in terms of dry weight is equivalent to 1 g of the extract solution) is preferably from approximately 0.01 to 5.0%. The concentration of ethinyl estradiol is preferably from approximately 0.001 to 0.1. The concentration of the extract solution of *Isodon japonica* Hara (1 g in terms of dry weight is equivalent to 1 g of the extract solution) is preferably from 0.01 to 10.0%. The concentration of the extract solution of the sophora root (1 g in terms of dry weight is equivalent to 1 g of the extract solution) is preferably from approximately 0.01 to 10.0%.

With respect to ingredients which are known to be effective in preventing the aging of skin by the suppressing the formation of peroxidated lipids, it is advisable that the concentration of an extract of a scutellaria root be from 0.01 to 10.0%, the concentration of vitamin E be from 0.1 to 5.0%, and the concentration of aloe extract be from 0.01 to 10.0%.

Examples of the skin-wetting agent include known skin wetting agents such as glycerin, propylene glycol, 1,3-butylene glycol, ethylene glycol, diethylene glycol, PEG (polyethylene glycol), ethylhexanediol, sugar alcohols (for example, sorbitol), and mucopolysaccharides (for example, hyaluronate salt, chondroitin sulfate and PCA salt) which are used in this field. The concentration of the skin-wetting agent is within the ordinary range. It is preferably within the range of from 0.1 to 10%.

Examples of the keratin softening agent include salicylic acid and urea. The concentration of the keratin softening agent is from 0.1 to 10%.

Examples of the anionic surfactant include N-lauroylglutamine hydrochloride. Examples of the nonionic surfactant include decaglyceryl monolaurate, polyoxyethylene sorbitan and polyoxyethylene-hardened castor oil. The concentration of the surfactant is preferably from 0.1 to 5.0%.

Examples of the base used in the hair-growth accelerator of this invention include bases which are generally employed in the external agent, such as a water-solubilizing agent and an alcohol solvent, common bases such as a cream, a gel cream and an ointment, makeup cosmetics such as a foundation and a lipstick, and washing and bathing products such as a shampoo, a rinse and a soap. The excellent effect of this invention can be fully observed with these bases.

Production Examples

A method for obtaining an extract of a plant of genus Euonymus is specifically illustrated hereinafter. It is however, not essential that this extraction method be employed.

Production Example 1

Leaves and stems of *Euonymus japonica* Thunb. were chopped with a mixer. The squeezed juice was filtered, and chlorophyll was removed from the filtrate with a centrifugal separator, followed by evaporating the water. The residue was used as an extract in this invention.

Production Example 2

Leaves and stems of *Euonymus alata* Sieb. which had been chopped were dipped in an equal amount of ethanol. The mixture was charged into a Soxhletis extractor, and extracted with ethanol for 8 hours while warming. Thereafter, the extract solution was cooled and filtered, and then the solvent was evaporated. The residue was used as an extract in this invention.

Production Example 3

Leaves and stems of *Euonymus japonica* Thunb. which had been chopped were dipped in an equal amount of a mixed solvent of propylene glycol and distilled water at a ration of 1:1. The dipping-extraction was performed batchwise for 24 hours while heating at 50° C. Then, the extract solution was cooled and filtered, and then the solvent was evaporated. The residue was used as an extract in this invention.

EXAMPLES

The present invention is illustrated further by referring to the following Examples. However, the present invention is not limited to these Examples.

The external agent of this invention may contain, in addition to the following ingredients, ingredients which have been so far effectively used for the skin and hair.

Example 1

According to the following recipe, a hair-growth gel product having an excellent effect to promote the growth of hair was prepared in a usual manner.

|  | (unit: g) |
|---|---|
| Extract of *Euonymus alata* Sieb. | 1.0 |
| 7-Chloro-3-methyl-2H-1,2,4-benzothiadiazine-1,1-dioxide | 1.0 |
| Conc. glycerin | 2.0 |
| Ethylhexanediol | 2.0 |
| Hinokitiol | 0.01 |
| Decaglyceryl monolaurate | 0.5 |
| Carboxyvinyl polymer | 0.5 |
| Triethanolamine | suitable amount |
| Flavor | suitable amount |
| Alcohol | 30.0 |
| Water* | total amount 100.0 |

*The total amount was adjusted to 100.0 g with the addition of water

Example 2

According to the following recipe, a hair-growth gel product having an excellent effect to grow hair was prepared in a usual manner.

|  | (unit: g) |
|---|---|
| Extract of *Euonymus Japonica* Thunb. | 1.5 |
| Conc. glycerin | 5.0 |
| Salicylic acid | 0.1 |
| POE-hardened castor oil (50 E.O.) | 0.5 |
| Alcohol | 30.0 |
| Flavor | trace amount |
| Buffer solution | suitable amount |
| Water* | total amount 100.0 |

*The total amount was adjusted to 100.0 g with the addition of water.
(POE means polyoxyethylene and E.O. means ethylene oxide.)

Example 3

According to the following recipe, a hair-growth lotion having an excellent effect for promoting the growth of hair was prepared in a usual manner.

|  | (unit: g) |
|---|---|
| 1,3-Butylene glycol extract of *Euonymus alata* Sieb. | 2.0 |
| Extract solution of a sophora root | 5.0 |
| Urea | 1.0 |
| β-Glycyrrhetic acid | 0.1 |
| Sodium N-lauroylglutamate | 0.5 |
| Flavor | trace amount |
| Buffer solution | suitable amount |
| Alcohol | 50.0 |
| Phenoxyethanol | 1.0 |
| Water* | total amount 100.0 |

*The total amount was adjusted to 100.0 g with the addition of water.

Example 4

|  | (unit: g) |
|---|---|
| Extract of *Euonymus radicons* Sieb. | 0.5 |
| Methyl ester of (3-carboxypropyl)-trimethylammonium chloride | 1.0 |
| Concentrated glycerin | 3.0 |
| Isopropylmethylphenol | 0.3 |
| Decaglyceryl monolaurate | 0.5 |
| Salicylic acid | 0.5 |
| Flavor | trace amount |
| Buffer solution | suitable amount |
| Alcohol | 40.0 |
| Water* | total amount 100.0 |

*The total amount was adjusted to 100.0 g with the addition of water.

Example 5

|  | (unit: g) |
|---|---|
| Extract of *Euonymus japonica* Thunb. | 1.0 |
| 6-Amino-1,2-dihydrohydroxyimino-4-piperidinopyrimidine | 1.0 |
| Concentrated glycerin | 25.0 |
| Salicylic acid | 0.5 |
| Polyoxyethylene-hardened castor oil (50 E.O) | 0.5 |
| Isopropylmethylphenol | 0.3 |
| Flavor | trace amount |
| Buffer solution | suitable amount |
| Alcohol | 60.0 |
| Water* | total amount 100.0 |

*The total amount was adjusted to 100.0 g with the addition of water.

Example 6

According to the following recipe, a hair-growth lotion having an excellent effect to promote the growth of hair was prepared in a usual manner.

|  | (unit: g) |
| --- | --- |
| Extract of *Euonymus alata* Sieb. | 5.0 |
| Sodium lauryl POE (3) sulfate | 30.0 |
| Sodium lauryl sulfate | 15.0 |
| Ethylene glycol monostearate | 3.0 |
| N-lauroyldiethanolamide | 2.0 |
| Lanoline derivative | 1.0 |
| Hydrolyzed keratin | 3.0 |
| Flavor | trace amount |
| Pigment | trace amount |
| Water* | total amount 100.0 |

*The total amount was adjusted to 100.0 g with the addition of water.

Example 7

According to the following recipe, a hair-growth cosmetic rinse having an excellent effect to promote the growth of hair was prepared in a usual manner.

|  | (unit: g) |
| --- | --- |
| Extract of *Euonymus japonica* Thunb. | 3.0 |
| Stearyl trimethylammonium chloride | 2.0 |
| Cetyl alcohol | 2.0 |
| Silicone oil | 3.0 |
| Oleyl POE (10) alcohol ether | 1.0 |
| Glycerin | 5.0 |
| Hydrolyzed keratin | 2.0 |
| Flavor | trace amount |
| Pigment | trace amount |
| Water* | total amount 100.0 |

*The total amount was adjusted to 100.0 g with the addition of water.

Example 8

According to the following recipe, a cosmetic cream having an excellent effect of preventing the aging of the skin and of beautifying the skin was produced.

|  | (unit: g) |
| --- | --- |
| Bees wax | 6.0 |
| Cetanol | 5.0 |
| Reduced lanoline | 8.0 |
| Squalane | 37.5 |
| Aliphatic acid glycerin | 4.0 |
| Monostearic acid glycerin | 2.0 |
| Polyoxyethylene sorbitan monolaurate (20 E.O.) | 2.0 |
| Extract of *Euonymus japonica* Thunb. | 2.0 |
| Flavor | suitable amount |
| Antiseptic and antioxidant | suitable amounts |
| Propylene glycol | 5.0 |
| Purified water | total amount 100.0 |

Example 9

According to the following recipe, a cosmetic cream having an excellent effect of preventing the aging of the skin and of beautifying the skin was produced.

<Example of a combination with other ingredients to prevent the aging of the skin>

|  | (unit: g) |
| --- | --- |
| Bees wax | 6.0 |
| Cetanol | 5.0 |
| Reduced lanoline | 8.0 |
| Squalane | 37.5 |
| Aliphatic acid glycerin | 4.0 |
| Monostearic acid glycerin | 2.0 |
| Polyoxyethylene sorbitan monolaurate (20 E.O.) | 2.0 |
| Extract of *Euonymus alata* Sieb. | 1.0 |
| Tocopherol acetate (ingredient to control skin aging) | 0.5 |
| Flavor | suitable amount |
| Antiseptic and antioxidant | suitable amounts |
| Propylene glycol | 5.0 |
| Purified Water | total amount 100.0 |

Example 10

According to the following recipe, a lotion having an excellent effect of preventing the aging of the skin and of beautifying the skin was prepared.

|  | (unit: g) |
| --- | --- |
| Glycerin | 5.0 |
| Propylene glycol | 4.0 |
| Oleyl alcohol | 0.1 |
| Polyoxyethylene sorbitan monolaurate (20 E.O) | 1.5 |
| Polyoxyethylene lauryl ether | 0.5 |
| Extract of *Euonymus radicons* Sieb. | 0.5 |
| Ethanol | 10.0 |
| Flavor | suitable amount |
| Antiseptic and antioxidant | suitable amounts |
| Purified Water | total amount 100.0 |

Example 11

According to the following recipe, a lipstick having an excellent effect of retaining moisture and of activating cells of lips was prepared.

|  | (unit: g) |
| --- | --- |
| Castor oil | 48.8 |
| Hexadecyl alcohol | 27.0 |
| Lanoline | 4.0 |
| Bees wax (yellow) | 5.0 |
| Ozocerite | 4.0 |
| Candelilla wax | 7.0 |
| Carnauba wax | 2.0 |
| Extract of *Euonymus japonica* Thunb. | 1.0 |
| Antiseptic and antioxidant | suitable amounts |
| Titanium oxide | 2.0 |
| Yellow #202 | 0.5 |
| Orange #211 | 0.2 |
| Flavor | suitable amount |

Test Example

One group consisted of from 4 to 7 healthy men who were from 35 to 51 years old and suffered from alopecia Praematura. A test solution was applied on their scalps at a dose of approximately 3 ml once or twice a day for 3 months. As a result, the following hair-growth effect was obtained.

(Evaluation Standard)

Three months later, the growth of new hair on the applied portion was evaluated by a hair-density measuring method in which the number of hair shaft of terminal hairs per unit area is counted, and a SCORE evaluation method in which the evaluation is performed through photography. The SCORE evaluation was based on the following standard.

SCORE 1: Almost no hair is seen, and only a few vellus hairs are observed.

SCORE 2: Many vellus hairs and a few terminal hairs are observed on a portion from which hairs have fallen out.

SCORE 3: Dense vellus hairs are observed on a portion from which hairs have fallen out, and terminal hair observed on approximately half of the portion.

SCORE 4: The whole portion is covered with terminal hairs, but scalp is visible through the terminal hairs.

SCORE 5: Neither a section from which hairs have fallen out nor vellus hairs are observed.

When the state of the hairs is improved by at least one rank according to the SCORE evaluation, the test solution is estimated to be "effective."

Results

1) The effectiveness of the hair-growth accelerator which was a skin external agent of this invention in which 1.0% of an ethanol extract of *Euonymus alata* Sieb. is contained in base 1 was 74.5%.

2) The effectiveness of the hair-growth accelerator in which 1.0% of methyl ester of (3-carboxypropyl)-trimethylammonium chloride and 0.5% of the ethanol extract of *Euonymus japonics* Thunb. were contained in a base 1 was 6.2% higher than that of the hair-growth accelerator in which 1.0% of methyl ester of (3-carboxypropyl)-trimethylammonium chloride was contained in base 1. Thus, the synergistic effect given by the ethanol extract of *Euonymus japonica* Thunb. was observed.

3) The effectiveness of the hair-growth accelerator in which 1.0% of 6-amino-1,2-dihydrohydroxyimino-4-piperidinopyrimidine and 0.5% of the ethanol extract of *Euonymus japonica* Thunb. were contained in a base 2 was 9.8% higher than that of the hair-growth accelerator in which 1.0% of 6-amino-1,2-dihydrohydroxyimino-4-piperidinopyrimidine was contained in base 2. Thus, the synergistic effect of the ethanol extract of *Euonymus japonica* Thunb. was observed.

4) The effectiveness of the hair-growth accelerator in which 1.0% of 7-chloro-3-methyl-2H-[benzo-1,2,4-thiadiazine]-1,1-dioxide and 1.0% of the ethanol extract of *Euonymus japonica* Thunb. were contained in base 3 was 12.1% higher than that of the hair-growth accelerator in which 1.0% of 7-chloro-3-methyl-2H-[benzo-1,2,4-thiadiazine]-1,1-dioxide was contained in base 3. Thus, the synergistic effect given by the ethanol extract of *Euonymus japonica* Thunb. was observed.

5) The effectiveness of the hair-growth accelerator in which 50% of polyoxyethylene sorbitan monostearate (20 E.O.) and 0.5% of the ethanol extract of *Euonymus japonica* Thunb. were contained in base 1 was 8.5% higher than that of the hair-growth accelerator in which 50% of polyxyethylene sorbitan monostearate (20 E.O.) was contained in base 1. Thus, the synergistic effect given by the ethanol extract of *Euonymus japonica* Thunb. was observed. Incidentally, the amount of water of the base was decreased by the amount of polyoxyethylene sorbitan monostearate (20 E.O.).

6) The effectiveness of the hair-growth accelerator in which 1.0% (equivalent to 1 g in terms of dry weight) of the extract solution of *Swertia japonica* Makino and 0.5% of the ethanol extract of *Euonymus japonica* Thunb. were contained in base 1 was 7.4% higher than that of the hair-growth accelerator in which 1.0% (equivalent to 1 g in terms of dry weight) of the extract solution of *Swertia japonica* Makino was contained in base 1. Thus, the synergistic effect given by the ethanol extract of *Euonymus japonica* Thunb. was observed.

7) The effectiveness of the hair-growth accelerator in which 0.1% of ethinyl estradiol and 0.5% of the ethanol extract of *Euonymus japonica* Thunb. were contained in base 1 was 6.9% higher than that of the hair-growth accelerator in which 0.1% of ethinyl estradiol was contained in base 1. Thus, the synergistic effect given by the ethanol extract of *Euonymus japonica* Thunb. was observed.

8) The effectiveness of the hair-growth accelerator in which 2.0% (equivalent to 2 g in terms of dry weight) of the extract solution of *Isodon japonica* Hara and 0.2% of the ethanol extract of *Euonymus japonica* Thunb. were contained in base 1 was 6.9% higher than that of the hair-growth accelerator in which 2.0% (equivalent to 2 g of dry weight) of the extract solution of *Isodon japonica* Hara was contained in base 1. Thus, the synergistic effect given by the ethanol extract of *Euonymus japonica* Thunb. was observed.

The compositions of the bases which were used to prepare the hair-growth accelerators subjected to the test are shown below.

|  | (unit: g) |
|---|---|
| Base 1: | |
| Conc. glycerin | 3.0 |
| Isopropylmethylphenol | 0.3 |
| Decaglyceryl monolaurate | 0.5 |
| Salicylic acid | 0.5 |
| Flavor | trace amount |
| Alcohol | 40.0 |
| Water | total amount 100.0 |
| Base 2: | |
| Conc. glycerin | 25.0 |
| Isopropylmethylphenol | 0.3 |
| Polyoxyethylene-hardened castor oil (50 E.O.) | 0.5 |
| Salicylic acid | 0.5 |
| Flavor | trace amount |
| Alcohol | 60.0 |
| Water | total amount 100.0 |
| Base 3: | |
| Conc. glycerin | 2.0 |
| Isopropylmethylphenol | 0.3 |
| Decaglyceryl monolaurate | 0.5 |
| Urea | 1.0 |
| Carboxyvinyl polymer | 0.5 |
| Triethanolamine | trace amount |
| Ethylhexanediol | 2.0 |
| Flavor | trace amount |
| Alcohol | 30.0 |
| Water | total amount 100.0 |

What is claimed is:

1. A topical hair growth agent comprising as an essential hair growth ingredient an extract of a plant of genus Euonymus in a cosmetically acceptable base, wherein (i) the plant is selected from the group consisting of *Euonymus japonica* Thunb., *Euonymus radicons* Sieb, *Euonymus japonicus* Thunb. var. aureovariegatus Lowe, *Euonymus japonicus* Thunb. var. longifolius Nakai, *Euonymus japonicus* f. macrophyllus Beiss., *Euonymus boninensis* Koidz., *Euonymus kawachinunus* Nakai, *Euonymus japonicus* f. microphyllus Rehd. and *Euonymus japonicus* Thunb. var. radicifer Nakai, (ii) the extract is obtained by contacting the plant with a solvent selected from the group consisting of t-butanol, propylene glycol, 1-3-butylene glycol, chloroform and diethylether, and (iii) the extract is present in an amount sufficient to activate skin and hair root cells for growing hair.

2. The topical hair growth agent according to claim 1, wherein the plant of genus Euonymus is *Euonymus japonica* Thunb. or *Euonymus radicons* Sieb.

3. The topical hair growth agent according to claim 2, wherein the extract is contained at 0.001 to 10% (w/w), in terms of dry weight (w).

4. The topical hair growth agent according to claim 1, formulated into a liquid, a cream, a gel cream, an ointment or a solid.

5. The topical hair growth agent according to claim 1, wherein the extract is obtained from plant parts selected from the group consisting of leaves, stems, roots and mixtures thereof of one or more plants of the genus Euonymus by chopping and forming into a semi-fluid liquid.

6. The topical hair growth agent according to claim 5, wherein the semi-fluid liquid is extracted with a solvent and a supernatant liquid obtained thereby is evaporated by freeze drying.

7. A method of activation of skin and hair root cells for stimulating growth of hair comprising topical application of an agent according to claim 1 under an application regimen sufficient to activate skin and hair root cells for growing hair.

8. A method of activation of skin and hair root cells for stimulating growth of hair comprising topical application of an agent according to claim 2 under an application regimen sufficient to activate skin and hair root cells for growing hair.

9. A method of activation of skin and hair root cells for stimulating growth of hair comprising topical application of an agent according to claim 3 under an application regimen sufficient to activate skin and hair root cells for growing hair.

10. A method of activation of skin and hair root cells for stimulating growth of hair comprising topical application of an agent according to claim 5 under an application regimen sufficient to activate skin and hair root cells for growing hair.

11. A skin external agent for retaining skin moisture and promoting hair growth comprising as an essential hair growth ingredient an extract of a plant of genus Euonymus in a base, wherein (i) the plant is selected from the group consisting of *Euonymus japonica* Thunb., *Euonymus radicons* Sieb, *Euonymus japonicus* Thunb. var. aureovariegatus Lowe, *Euonymus japonicus* Thunb. var. longifolius Nakai, *Euonymus japonicus* f. macrophyllus Beiss., *Euonymus boninensis* Koidz., *Euonymus kawachinunus* Nakai, *Euonymus japonicus* f. microphyllus Rehd. and *Euonymus japonicus* Thunb. var. radicifer Nakai, (ii) the extract is obtained by contacting the plant with a solvent selected from the group consisting of t-butanol, propylene glycol, 1-3-butylene glycol, chloroform and diethylether, and (iii) the extract is present in an amount sufficient to retain skin moisture.

12. The skin external agent according to claim 11, wherein the plant of genus Euonymus is *Euonymus japonica* Thunb. or *Euonymus radicons* Sieb.

13. The skin external agent according to claim 11, formulated into a liquid, a cream, a gel cream, an ointment or a solid.

14. A topical hair growth agent comprising (i) an extract of a plant of genus Euonymus in a cosmetically acceptable base, and (ii) a secondary hair growth promoting constituent, wherein the plant is selected from the group consisting of *Euonymus japonica* Thunb., *Euonymus radicons* Sieb, *Euonymus japonicus* Thunb. var. aureovariegatus Lowe, *Euonymus japonicus* Thunb. var. longifolius Nakai, *Euonymus japonicus* f. macrophyllus Beiss., *Euonymus boninensis* Koidz., *Euonymus kawachinunus* Nakai, *Euonymus japonicus* f. microphyllus Rehd. and *Euonymus japonicus* Thunb. var. radicifer Nakai.

15. The topical hair growth agent according to claim 14, wherein the extract is contained at 0.001 to 10% (w/w), in terms of dry weight (w).

16. The topical hair growth agent according to claim 14, formulated into a liquid, a cream, a gel cream, an ointment or a solid.

17. A method of activation of skin and hair root cells for stimulating growth of hair comprising topical application of an agent according to claim 14 under an application regimen sufficient to activate skin and hair root cells for growing hair.

18. A method for activating skin and hair root cells so as to stimulate the growth of hair comprising topically applying an extract of a plant selected from the group consisting of *Euonymus japonica* Thunb,, *Euonymus radicons* Sieb, *Euonymus japonicus* Thunb. var. aureovariegatus Lowe. *Euonymus japonicus* Thunb. var. longifolius Nakai, *Euonymus japonicus* f. macrophyllus Beis., *Euonymus boninensis* Koidz., *Euonymus kawachinunus* Nakai, *Euonymus japonicus* f. microphyllus Rehd. and *Euonymus japonicus* Thunb. var. radicifer Nakai, dispersed in a cosmetically acceptable base, to an area of skin where the growth of hair is desired, with the extract applied in accordance with an application regimen effective to activate skin and hair root cells and promote the growth of hair.

19. The method of stimulating the growth of hair according to claim 18, wherein the extract is obtained by contacting the plant with a solvent selected from the group consisting of t-butanol, propylene glycol, 1-3-butylene glycol, chloroform and diethylether.

20. The topical hair growth agent of claim 14 wherein the secondary hair growth promoting constituent is selected from the group consisting of methyl ester of (3-carboxypropyl)-trimethylammonium chloride, 6-amino-1,2-dihydrohydroxyimino-4-piperidinopyrimidine, 7-chloro-3-methyl-2H-benzo-1,2,4-thiadiazine-1,1-dioxide, polyoxyethylene sorbitan monostearate (20 E.O.), an extract solution of *Swertia japonica* Makino, ethinyl estradiol, an extract solution of *Isodon japonica* Hara. and an extract solution of a sophora root.

21. The topical hair growth agent according to claim 14, wherein the extract is contained as 0.01 to 5% (w/w) in terms of dry weight (w).

* * * * *